(12) United States Patent
Wang et al.

(10) Patent No.: US 8,968,172 B2
(45) Date of Patent: Mar. 3, 2015

(54) HANDHELD CELL EXCITATION TERMINAL CAPABLE OF DYNAMIC OPTIMIZATION OF THERAPEUTIC EFFECT AND REMOTE THERAPEUTIC SYSTEM

(75) Inventors: Jian Wang, Cupertino, CA (US); Edmond Ku, Cupertino, CA (US)

(73) Assignee: Biomobie Corporation, Cupertino, CA (US)

( * ) Notice: Subject to any disclaimer, the term of this patent is extended or adjusted under 35 U.S.C. 154(b) by 530 days.

(21) Appl. No.: 13/226,245

(22) Filed: Sep. 6, 2011

(65) Prior Publication Data

US 2012/0253101 A1    Oct. 4, 2012

(30) Foreign Application Priority Data

Apr. 2, 2011    (CN) .......................... 2011 1 0083275

(51) Int. Cl.
*A61N 1/00*    (2006.01)
*A61N 2/00*    (2006.01)
*A61N 2/02*    (2006.01)

(52) U.S. Cl.
CPC .. *A61N 2/004* (2013.01); *A61N 2/02* (2013.01)
USPC ................................. 600/14; 600/9

(58) Field of Classification Search
CPC .................................. A61N 2/02; A61N 1/40
USPC .......................... 600/9–15; 607/45, 46, 59, 62
See application file for complete search history.

(56) References Cited

U.S. PATENT DOCUMENTS

| | | | |
|---|---|---|---|
| 4,315,503 A | | 2/1982 | Ryaby et al. |
| 6,029,084 A * | | 2/2000 | Long et al. .................. 607/2 |
| 7,740,574 B2 * | | 6/2010 | Pilla et al. .................. 600/13 |
| 8,029,432 B2 | | 10/2011 | Dennis et al. |
| 8,376,925 B1 * | | 2/2013 | Dennis et al. .................. 600/14 |
| 2003/0130709 A1 | | 7/2003 | D.C. et al. |
| 2003/0158583 A1 | | 8/2003 | Burnett et al. |
| 2004/0077923 A1 | | 4/2004 | Frimerman et al. |
| 2005/0288744 A1 | | 12/2005 | Pilla et al. |
| 2006/0258896 A1 * | | 11/2006 | Haber et al. .................. 600/9 |
| 2008/0208284 A1 | | 8/2008 | Rezai et al. |
| 2009/0030476 A1 | | 1/2009 | Hargrove |
| 2009/0240310 A1 | | 9/2009 | Kennedy |
| 2010/0010288 A1 * | | 1/2010 | Von Ohlsen et al. .............. 600/9 |

(Continued)

FOREIGN PATENT DOCUMENTS

WO    WO-9632158 A1    10/1996

OTHER PUBLICATIONS

Co-pending U.S. Appl. No. 13/269,548, filed Oct. 7, 2011.

(Continued)

*Primary Examiner* — Charles A Marmor, II
*Assistant Examiner* — Carrie R Dorna
(74) *Attorney, Agent, or Firm* — Perkins Coie LLP

(57) ABSTRACT

A cell excitation terminal and a therapeutic system using customized electromagnetic (EM) waves varying dynamically with time for excitation include one or more EM wave generators, each of the EM wave generators is connected to a central processing unit (CPU), and the CPU controls, according to a signal detected by a human body status detection device, the EM wave generator to send EM waves corresponding to a detected subject. The therapeutic system can perform remote management. A remote server optimizes and updates therapeutic waveforms of a patient constantly according to a therapeutic effect of the patient, thereby improving the therapeutic effect constantly.

20 Claims, 13 Drawing Sheets

(56) References Cited

U.S. PATENT DOCUMENTS

2010/0057655 A1* 3/2010 Jacobson et al. ............... 706/45
2011/0065976 A1 3/2011 Chornenky et al.

OTHER PUBLICATIONS

International Search Report and Written Opinion PCT/US2011/055487 dated May 30, 2012, 16 pages.

* cited by examiner

| | Sickness | Therapeutic waveform | Therapeutic means (manner) |
|---|---|---|---|
| I<br>Heart disease | Heart disease A1 | Waveform P1 | Time T1 |
| | Heart disease A2 | Waveform P1+waveform P3 | Time T2+cycle S1 |
| II<br>High blood pressure | Hypertension B1 | Waveform P4 | Time T3 |
| | Hypertension B2 | Waveform P5+waveform P6 | Time T4+cycle S2 |
| | Hypertension B3 | Waveform P6+waveform P7+waveform P8 | Time T4+cycle S3 |

FIG. 6

| Tested person | Symptoms | Testing scheme | Time and times for testing | Assessment of the test | Scheme/therapeutic effect feasibility |
|---|---|---|---|---|---|
| Yao ** | Headache caused by catching a code at the head | Bio A aching part radiation | The test time span is 1.5 hours, and includes 6 times | Symptoms disappeared | Obviously effective |
| Bai ** | Lumbago | $A_{100}$ local radiation | The test time span is 1 day, and includes 1 time | Symptoms alleviated | Obviously effective |
| Chen ** | Insomnia | $A_{50}$ radiation on palm | The test time span is 30 days, and includes 7 times | Symptoms obviously alleviated | Obviously effective |
| Wang ** | Dried blood, and empty felt at stomachs | Biologic energy level 5 and $A_{50}$ local radiation | The test time span is 19 days, and includes 33 times at the biologic energy level 5 and 15 times of $A_{50}$ | Emptiness remained unchanged at the biologic energy level 5, and the emptiness disappear at $A_{50}$ | Ineffective at the biologic energy level 5, and obviously effective at $A_{50}$ |
| Bai ** | lumbago for days | $A_{100}$ local aching point radiation | Totally once | Aching was alleviated after one hour, and aching did not occur the next day | Obviously effective |
| Wang ** | A part of the left instep near the ankle has ached for two days | $A_{50}$ local aching point radiation | The test time span is 6 days, and includes 24 times | Aching was alleviated on the first day, discomfort was not felt for consecutive days, but curing was not achieved, the aching disappeared the sixth day | Obviously effective |
| Bai ** | Palpitation, a too high heart rate | $A_{100}$ radiation on the acupuncture point Laogong of the palm | The test time span is 1 days, and includes 2 times | Symptoms disappeared | Obviously effective |
| Ren ** | Bloodshot fundus of the eye | Bio D local radiation | Totally two times, and 8 minutes for each time | Bloodshot fundus is alleviated for the first time, and symptoms disappeared after two times | Cured |
| Ren ** | Narrow right carotid | Bio C radiation on right carotid and left hand radial artery | The test time span is 46 days, and includes 72 times at the right carotid and 35 times at the left hand radial artery | The right carotid grows from 6.3 mm to 7.2 mm, and no other discomfort was felt | Obviously effective |

FIG. 8

Comparison of blood before and after therapy
Comparison before and after $A_{10}$ test
Zhao ** (Female)
Tested part: Neiguan    Time: 8 minutes
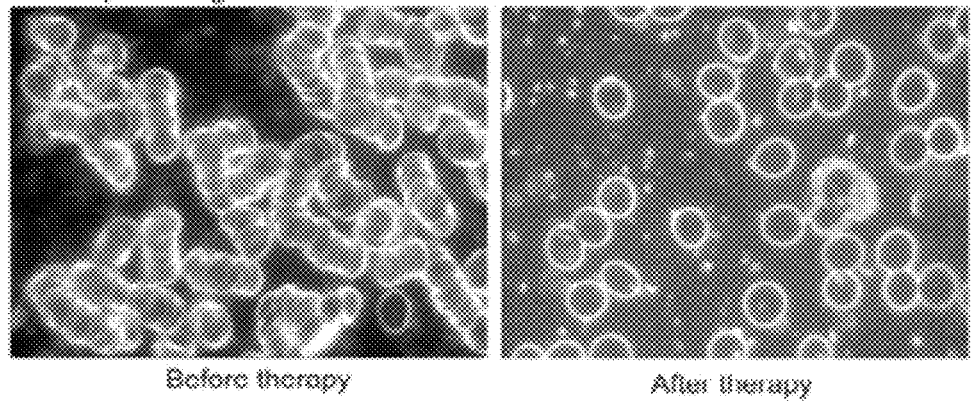
Before therapy                After therapy
Yang ** (Female)
Tested part: Neiguan    Time: 8 minutes
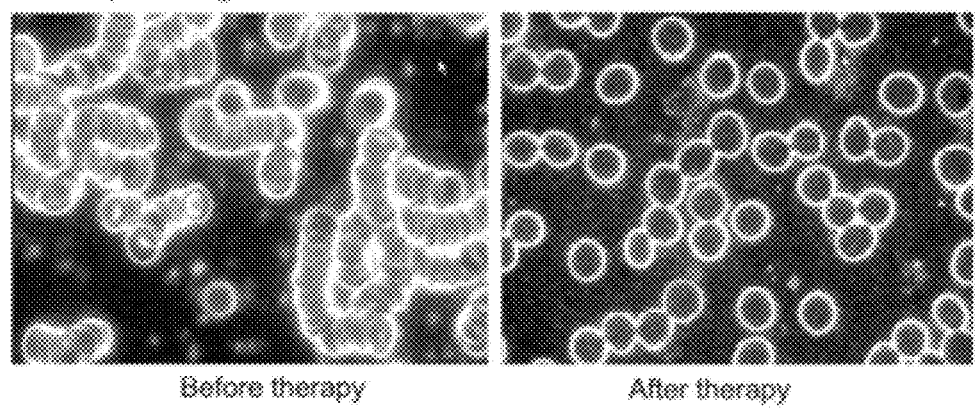
Before therapy                After therapy
Mr. Xu (Male)
Tested part: acupuncture point Laogong of the palm    Time: 8 minutes
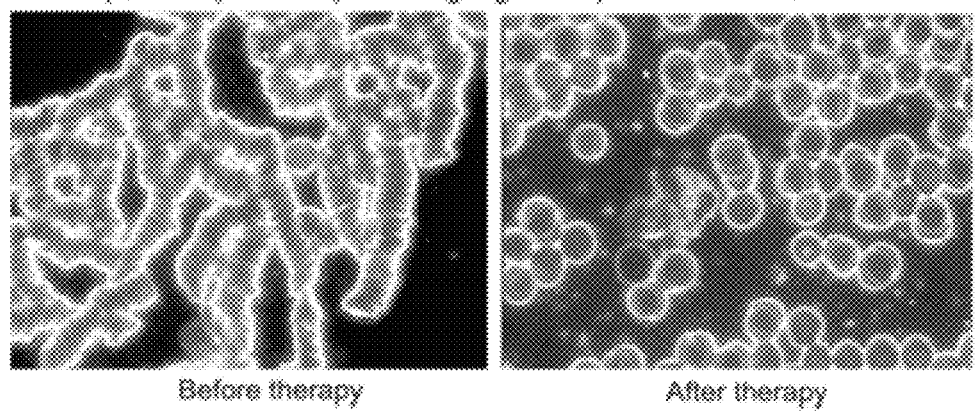
Before therapy                After therapy
*FIG. 9a*

Comparison of blood before and after therapy
Comparison before and after $A_{80}$ test

Wang  (Male)**
Tested part: acupuncture point Laogong of the palm    Time: 8 minutes

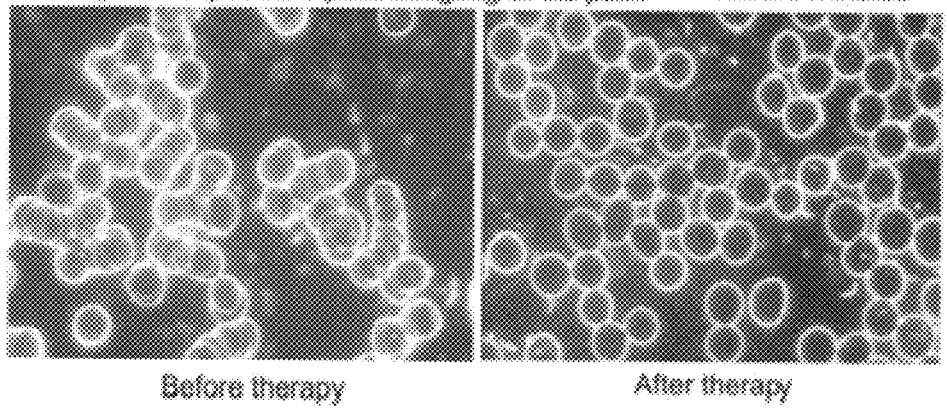

Before therapy — After therapy

Mr. Li (Male)
Tested part: acupuncture point Laogong of the palm    Time: 8 minutes

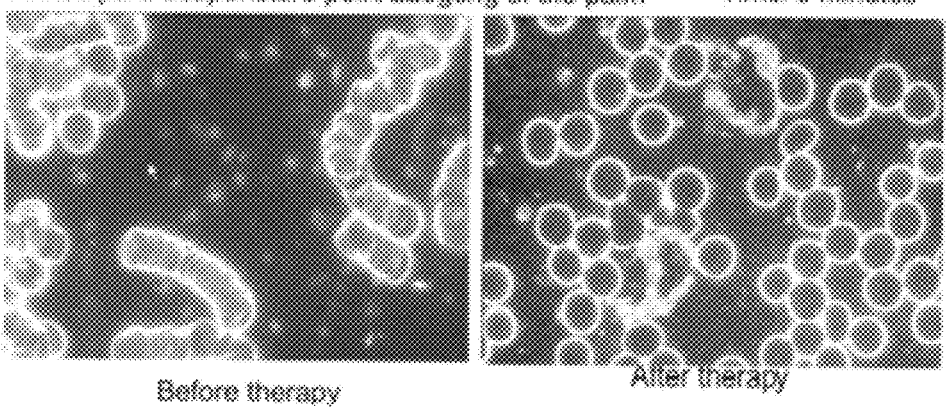

Before therapy — After therapy

Bai  (Female)**
Tested part: acupuncture point Laogong of the palm    Time: 8 minutes

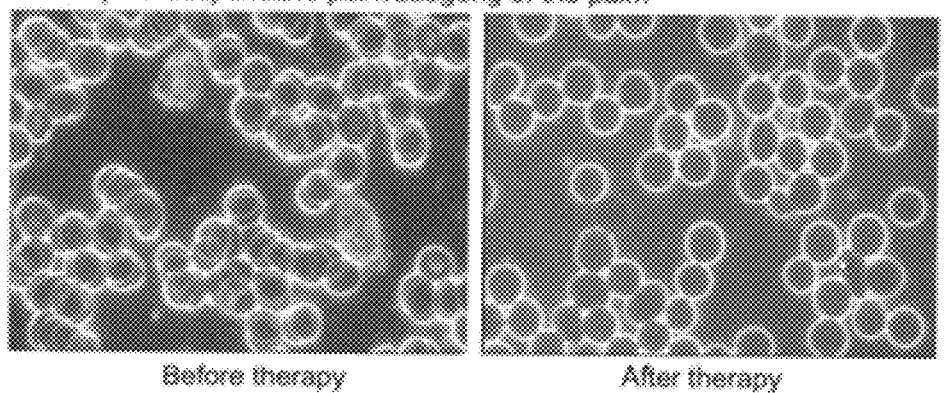

Before therapy — After therapy

*FIG. 9b*

HANDHELD CELL EXCITATION TERMINAL CAPABLE OF DYNAMIC OPTIMIZATION OF THERAPEUTIC EFFECT AND REMOTE THERAPEUTIC SYSTEM

This application claims the priority Chinese Patent Application No. CN 201110083275 filed 2 Apr. 2011 entitled and naming inventors Jian ("Jack") Wang and Edmond Ku, which application is incorporated herein by reference in its entirety.

BACKGROUND OF THE INVENTION

1. Field of the Invention

The present invention relates to a handheld cell excitation terminal capable of dynamic optimization of a therapeutic effect and a remote therapeutic system, in which the cell excitation terminal can perform direct therapy on a human body, and can be used in combination with other devices of the system through a wireless network, so as to perform useful therapy on a human body remotely.

2. Related Art

Currently, conventional needle-based therapeutic methods of acupuncture already exist, in which acupuncture needles are inserted into areas of or near meridians.

Furthermore, systems enabling a human body to be bathed in electromagnetic (EM) radiation have been available, so as to attempt a useful therapeutic effect on the human body with the intention of achieving the useful therapeutic effect similar to that of the conventional needle-based therapeutic methods. The systems have not yet employed electromagnetism on specific parts, such as meridians.

The conventional systems, equipment, therapeutic methods, and platforms do not select locations where an EM field (EMF) is applied, since they bathe a user in the EMF or are positioned in uncomfortable locations by a patient. They usually do not include a sensor device for helping a user or patient determine most suitable locations, or are likely to select unsuitable or improper non-optimized EM or magnetic characteristics to perform therapy, thereby possibly resulting in waste of optimal therapeutic periods.

For example, a Chinese invention patent with the application number being 200810010145.4 discloses a high-energy biological field effect therapeutic apparatus, in which a power circuit is disposed, an output of the power circuit is connected to a sampling amplifier circuit, an output of the sampling amplifier circuit is connected to a pulse generation circuit, an output of the pulse circuit is connected to a power amplifier circuit, an output of the power amplifier circuit is connected to the sampling amplifier circuit through a voltage regulator circuit on one path and connected to an indicator circuit on another path, and an output end of the indicator circuit is disposed with electrodes A and B. Output EM waves adjusted by a voltage ranging from 35 V to 220 V can rapidly open up human body meridians, activate blood, eliminate stasis, expel wind and cold, and adjust the balance of yin and yang among human organs, so as to adjust electric potential differences between human cells, and change structural arrangement of cells and molecules from orderless to orderly; adjust endocrine of the human body, and achieve the acid-base balance of the human body; and decrease the blood viscosity, soften blood vessels, improve the cerebral blood flow, and enhance immunity ability and self-healing ability of the human body, thereby enabling the human body to achieve an optimal state.

A Chinese invention patent with the application number being 200620031025.9 provides a health-care therapeutic apparatus having a wide EM spectrum, main characteristics of which are as follows. A mainframe is disposed in a middle portion of a cover body, and a spectrum therapeutic device is disposed on the cover body, and the spectrum therapeutic device involves a red spectrum an infrared spectrum. A low-intermediate frequency generator, a spectrum generator, and a control panel are disposed in the mainframe, and are connected to a low-intermediate frequency therapeutic device and a spectrum therapeutic device respectively. The infrared spectrum, the red spectrum, and the low-intermediate frequency spectrum are combined together perfectly, so that in a shared therapeutic range the three spectrums each perform better in the company of others, complement each other, and share resources, thereby realizing functions such as enhancing blood circulation of the human body, activating cells, improving immunity ability, and adjusting the nervous system.

The existing or claimed ones in the market only provide a static magnetic field, in which waveforms vary regularly with time. The waveforms are repeated, and cannot be modified or adjusted dynamically accordingly by sensing a sick body. The systems can support EMFs of different intensity or amplitudes, but if pulse systems only use the same waveform, a single waveform used by the same single-waveform systems and equipment is a general or non-optimized waveform, and therapeutic means and manners are not diversified, the systems are not applicable in cases in which types of patients are different, symptoms of patients are different, and patients are users.

SUMMARY OF THE INVENTION

The present invention is directed to a therapeutic system using customized EM waves varying dynamically with time for excitation, which uses bioelectromagnetic waves corresponding to expected physical status of a receiver to perform radiation on a specific part of the receiver.

In order to achieve the objective, the present invention provides a handheld cell excitation terminal capable of dynamic optimization of a therapeutic effect, which includes:
a central processing unit (CPU);
a human body status detection device connected to the CPU and used to detect human body status information;
one or more EM wave generators, where each of the EM wave generators is connected to the CPU, and the CPU controls, according to a signal detected by the human body status detection device, the bioelectromagnetic wave generator to send bioelectromagnetic waves corresponding to a detected subject; and
a power device, used to supply power to the devices.

The present invention further provides a remote medical system using customized EM waves varying dynamically with time for excitation, which includes:
a CPU;
a cell excitation terminal, where the cell excitation terminal includes:
a human body status detection device, used to detect human body status information;
a device for communication with the outside;
one or more bioelectromagnetic wave generators, where each of the EM wave generators is connected to the CPU, and the CPU controls, according to a signal detected by the human body status detection device, the bioelectromagnetic wave generator to send bioelectromagnetic waves corresponding to a detected subject; and
a power device, used to supply power to the devices,
a server, where the server is connected to the cell excitation terminal through a wireless network, receives and processes the human body status detection information sent by the cell excitation terminal, and sends an instruction, so that the CPU of the cell excitation terminal controls the bioelectromagnetic wave generator to send the bioelectromagnetic waves corresponding to the detected subject.

Furthermore, the server includes a database, used to store the detected human body status information, other associated therapeutic information, various therapeutic waveforms, and a mapping relationship list of patient sickness and waveforms, the mapping relationship list lists therapeutic bioelectromagnetic waves or bioelectromagnetic wave combinations and therapeutic means corresponding to different human body status.

Furthermore, the server further includes an optimization module, capable of updating the mapping relationship list of patient sickness and waveforms from time to time, so as to update the relationship list with optimal therapeutic bioelectromagnetic waves.

The EMF may be a pulsed EMF (PEMF).

The cell excitation terminal includes a power monitoring device, sending out a signal to call attention to power supplement, when the power is not enough.

Furthermore, the bioelectromagnetic wave generator includes a waveform multiplexer, selecting corresponding bioelectromagnetic waves from the stored in a server for processing and outputting several required bioelectromagnetic waves being the same or different.

The human body status detection device includes a heartbeat detector.

The human body status detection device includes a blood pressure detector.

The human body status detection device includes a motion sensor.

Furthermore, the bioelectromagnetic wave generator includes a drive circuit, receiving a waveform signal from a waveform shaper generator and driving an EM oscillating circuit to generate corresponding bioelectromagnetic waves.

The cell excitation terminal includes a digital-analog (D/A) converter, receiving a digital signal from the CPU and outputs an analog signal to the waveform shaper generator.

The present invention provides the portable therapeutic system using customized bioelectromagnetic waves varying dynamically with time for excitation, which is used to sense realtime physical status of a patient, for example a blood pressure, a heartbeat or pulse frequency, timely perform changing or replacement by using a different or modified EM pulse or EM pulse combination according to the physical status information, perform radiation on a part, for example a specific part, of a human body in a manner (for example for a period of time), and can modify an EMF, or modify only a magnetic field, or modify only an electric field according to a response of the patient to the EMF, so as to achieve a desired effect, thereby further improving the therapeutic effect. Furthermore, the therapeutic system according to the present invention can perform remote management. The remote server optimizes and updates therapeutic waveforms of a patient constantly according to a therapeutic effect of the patient, so as to be adapted for different patients or different physical status of a patient in different time, thereby improving the therapeutic effect constantly.

BRIEF DESCRIPTION OF THE DRAWINGS

FIG. 6 is an embodiment of a mapping relationship list of patient sickness and waveforms according to the present invention;

FIG. 8 is a measurement table of therapeutic effects of the waveform in FIG. 7 in respect of various sickness;

FIG. 9A and FIG. 9B are comparison diagrams of effects on blood before and after a therapeutic scheme according to the present invention is implemented.

DETAILED DESCRIPTION OF THE INVENTION

Embodiments of the present invention are described below in detail with reference to the accompanying drawings.

Figure 1:
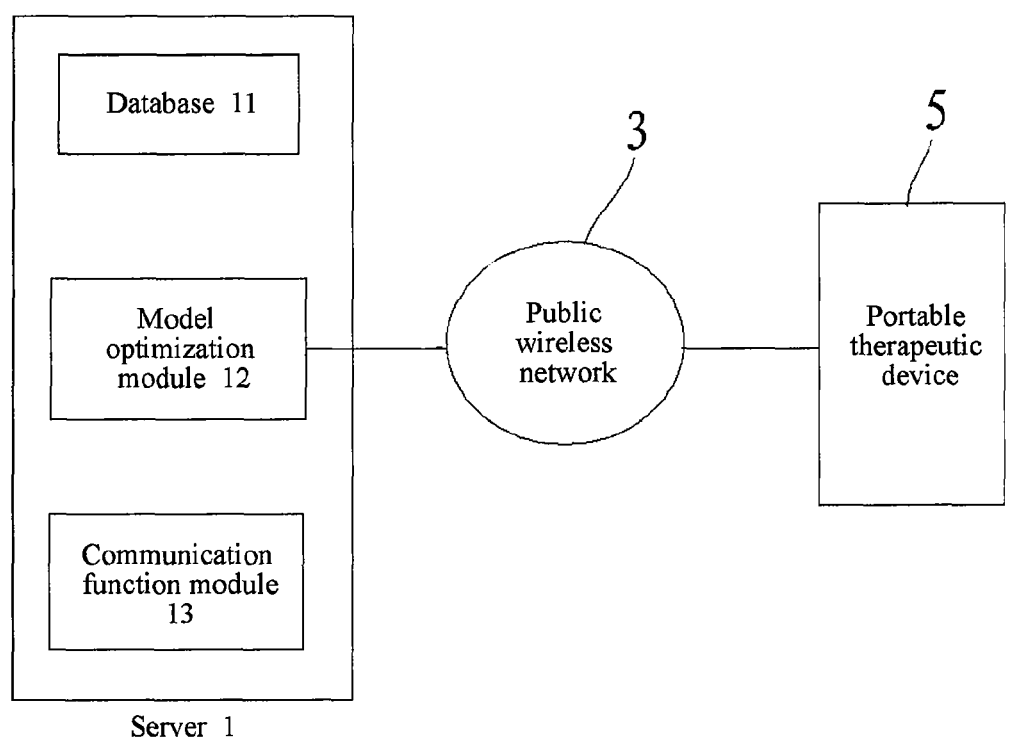
FIG. 1 is a schematic view of a remote therapeutic system using customized EM waves varying dynamically with time for excitation.

Referring to FIG. 1, the present invention provides a remote therapeutic system using customized bioelectromagnetic waves varying dynamically with time for excitation, which includes a server 1 and a cell excitation terminal 5. The server 1 is connected to the cell excitation terminal 5 through a public wireless network 3. The public wireless network 3 may be a common wireless communication network or Internet. The server 1 may be a public service platform, and can provide services for multiple patients or users at the same time. The server 1 includes a database 11 and an optimization module 12. The cell excitation terminal 5 is a micro therapeutic apparatus, can be conveniently fixed on a part of a human body and perform therapy (EM radiation) on the part, and can be used as a part of the remote therapeutic system or separately. The server 1 is connected to the public wireless network 3 through a communication function module 13.

Figure 2:
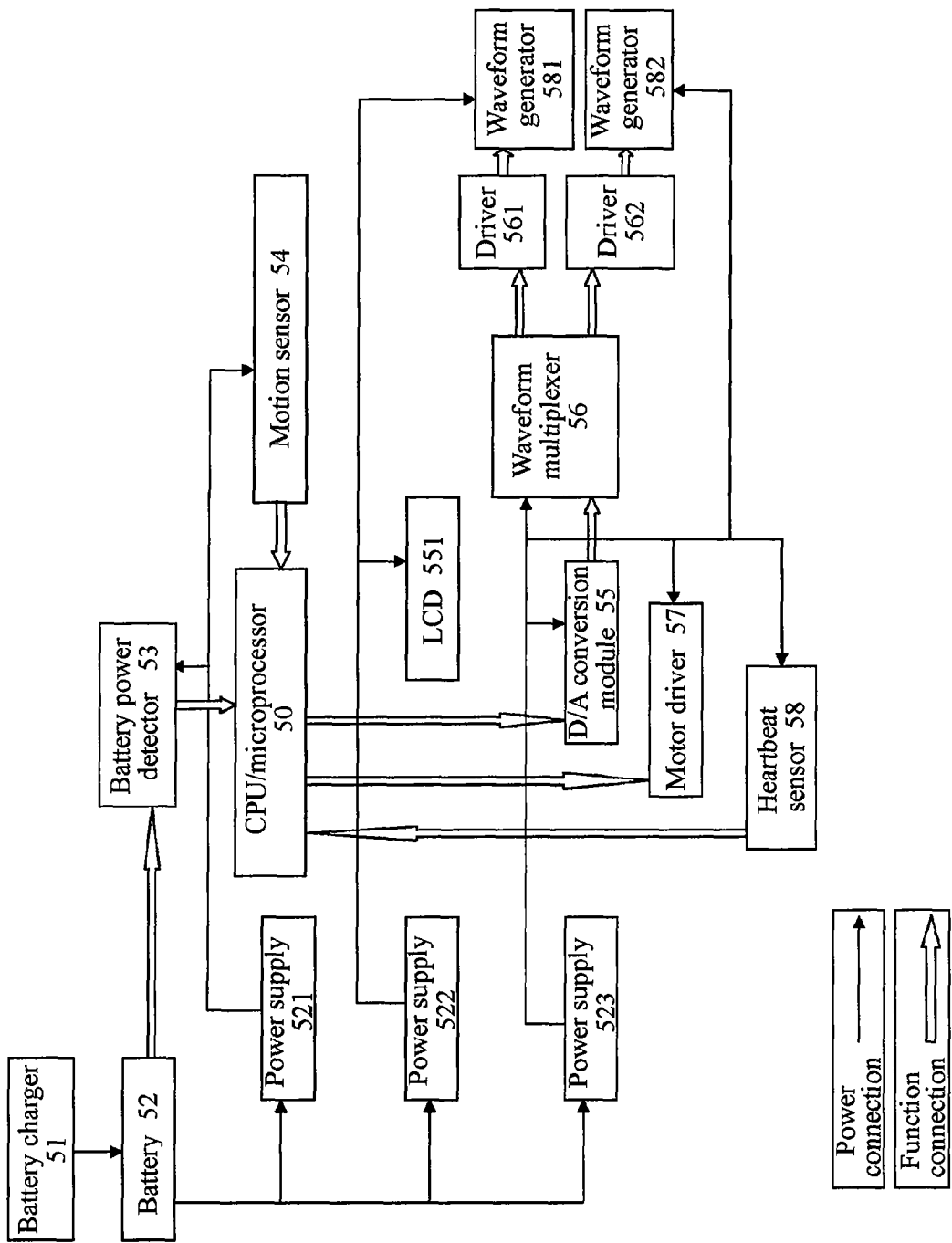
FIG. 2 is a schematic view of an embodiment of a cell excitation terminal of the remote therapeutic system using customized EM waves varying dynamically with time for excitation according to the present invention.

Referring to FIG. 2, the cell excitation terminal 5 according to the present invention includes a CPU 50, a human body status detection device connected to the CPU 50 and used to monitor human body status, a device for communication with the outside, one or more bioelectromagnetic wave generators, and a power device for providing the devices with power. Each of the bioelectromagnetic wave generators is connected to the CPU, and the CPU 50 controls, according to a signal detected by the human body status detection device, the bioelectromagnetic wave generator to send bioelectromagnetic waves corresponding to a detected subject.

In this embodiment, the device for communication with the outside is not shown in FIG. 2, and is a common communication device, for example, an antenna and a relevant communication module of a mobile phone connected to the wireless communication network, or a wired or wireless network connecting device connected to Internet. The power device adopts a battery, for example a common lithium battery, and includes a battery charger 51, a battery 52, and power supply modules 521, 522, and 523. The battery charger 51 can charge the battery 52 to guarantee continuous supply of power of the battery 52. The battery 52 supplies power to components required to be powered of the cell excitation terminal through the power supply modules 521, 522, and 523 respectively. The battery charger 51 is connected to external power through a power connection port 531, so as to perform charging.

The EM wave generator is formed by a waveform multiplexer 56, drivers 561 and 562, and waveform generators 581 and 582 connected to the drivers 561 and 562. The waveform multiplexer 56 is also common equipment in the market, receives multiple digital signals representing waveforms input by a D/A conversion module 55, and processes and converts the digital signals into multiple required analog signals. In this embodiment, two sets of EM wave output equipment are included. The waveform multiplexer 56 can output two waveform analog voltage signals that are input to the drivers 561 and 562 respectively. The drivers 561 and 562 respectively drive the waveform generators 581 and 582 to generate the corresponding bioelectromagnetic waves. The waveform generators 581 and 582 may adopt coil inductors to generate EM waves of a certain voltage. In this embodiment, EM waves in two paths are generated, and the two kinds of EM waves may have the same waveform or different waveforms. In addition, also according to needs, it may be designed to generate EM waves in one path or more than two paths, and one or more drivers may be designed. The waveform generators 581 and 582 are set by configuring to be able to use a relatively low-frequency pulsed magnetic field to stimulate blood circulation in a body of a patient. The low frequency normally ranges from 10 Hz to 200 Hz, typically ranges from 20 Hz to 120 Hz, more typically ranges from 20 Hz to 40 Hz, and is about or actually 30 Hz (for example, 30±3 Hz) in a specific case.

The central control unit 50 is a control center of the cell excitation terminal, controls working of the components, and may adopt a control unit such as a microprocessor or a single-chip microcomputer. The D/A conversion module 55 can convert digital signals representing waveforms and sent by the central control unit 50 into analog signals, so that the waveform multiplexer 56 receives the analog signals to work.

In this embodiment, the human body status detection device adopts a heartbeat sensor 58 and a motion sensor 54. The heartbeat sensor 58 can measure a heart rate of a human body, and input the heart rate to the central control unit 50. The motion sensor 54 can timely measure motion features, such as vibration and acceleration of a human body, for example, how the motion goes on and motion characteristics thereof within a period of time. Motion data of the period of time is analyzed and processed to acquire data of part of other physical status of the human body. The central control unit 51 may determine current physical status of a patient according to parameters of the heartbeat and the part of the other physical status, and determine a required therapeutic EM waveform or waveform combination and a therapeutic manner, so as to send control signals (digital signals representing waveforms) to the waveform multiplexer 56 and the drivers 561 and 562, so that the waveform generators 581 and 582 respectively generate a determined EM wave or EM wave combination to perform radiation therapy on the patient according to the determined manner. Similarly, the human body status detection device for measuring the physical status of the human body may also be a blood pressure detector or sensor, a human body blood viscosity detection device, an electroencephalogram (EEG) measurer, an electrocardiogram (ECG) measurer, or other apparatuses or devices capable of detecting the physical status of the human body conveniently and timely. One or more of the apparatus or devices may be used to provide a set of data of the human body status. In the present invention, it is found by research that it is fairly reliable to select a therapeutic scheme according to the motion features, such as the vibration and acceleration, of the human body measured by the motion sensor 54.

The motion sensor 54 may adopt a motion accelerometer. The accelerometer is a highly sensitive motion sensor. When a patient or a user holds the device by hand and stays still, the sensor detect most small vibrations (such as heartbeats and blood flow pulses) in the human body, a heart rate spectrum of the patient is embedded in a vibration signal, detected signals are input to the central control unit 50, and the heat rate spectrum or pulses of the user are detected and extracted from all of the signals through digital signal processing (DSP) technologies.

Figure 3:
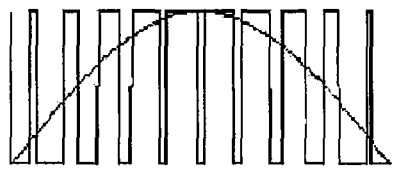
FIG. 3 illustrates a pulse width modulation (PWM) waveform with a duty factor (black) varying with time.

Many methods may be used to generate different bioelectromagnetic waveforms. FIG. 3 illustrates a PWM waveform with a duty factor (black) varying with time, and illustrates a sine wave (a smooth line) formed after low-pass filtering. Multiple kinds of waveforms may be waveforms generated by mixing a PWM basic waveform with a low-pass or even high-pass filtered wave. Definitely, a D/A system may be used to form the waveform, and the use of the PWM is not a must. The PWM is only a manner to realize a D/A function.

The central control unit 50 can send human body status information to the server 1 through the device for communication. The central control unit 50 can customize a bioelectromagnetic waveform suitable for a specific patient based on the human body status information and other physical status parameter data stored in the database 11 and according to factors, such as human body associated therapeutic information, such as therapeutic history, a sick body and/or therapeutic electrical properties on the sick body, and locations (meridian points), and other specific factors, such as skin thickness, amount of fact and tissue under therapeutic locations, a normal heart rate, and/or other physical factors. The technical feature is a core of the present invention.

A liquid crystal display (LCD) 551 is used to display a working state of the whole cell excitation terminal or working parameters of each relevant component.

A function connection port 532 is used for external connection, so as to input data or download a program from the outside, thereby enabling functional components involving, for example game, clock, and communication, to work.

The power connection port 531 is used to connect the power to supply the power.

A battery power detector 53 is used to monitor a power use situation of the whole system.

A motor driver 57 receives a signal sent by the central control unit 50, and meanwhile receives information transferred from the waveform multiplexer 56, so as to drive the whole system to operate.

Referring to FIG. 1 and FIG. 2, the cell excitation terminal 5 and the server 1 communicate through the public wireless network, thereby forming a complete therapeutic system. The server 1 includes the following functional modules.

(1) The database 11. The database 11 is used to store various therapeutic waveforms, a mapping relationship list of patient sickness and waveforms, human body status information, and other physical status parameters.

(2) The model optimization module 12. The model optimization module 12 performs filtering on therapeutic schemes constantly according to therapeutic effects within a certain period of time in respect of various sickness of one or different patients to select a preferred scheme, so as to optimize the mapping relationship list of patient sickness and waveforms constantly. The constant optimization process of the list can guarantee that the therapy can always achieve preferred effects, which is another important feature of the present invention. Implementation of the optimization manner may also be performed by persons skilled in the art designing relevant software or hardware according to the aforementioned process.

(3) The communication function module 13. The communication function module 13 communicates with the cell excitation terminal 5 through the public wireless network 3. A cell phone (mobile phone) may also be usefully used as the module or a bridge for connection. The cell phone can forward the information received by the server 1 to the cell excitation terminal 5 through a local radio frequency (RF) channel, that is, bluetooth, wireless fidelity (WiFi), or other wired or wireless connection.

Figure 4:
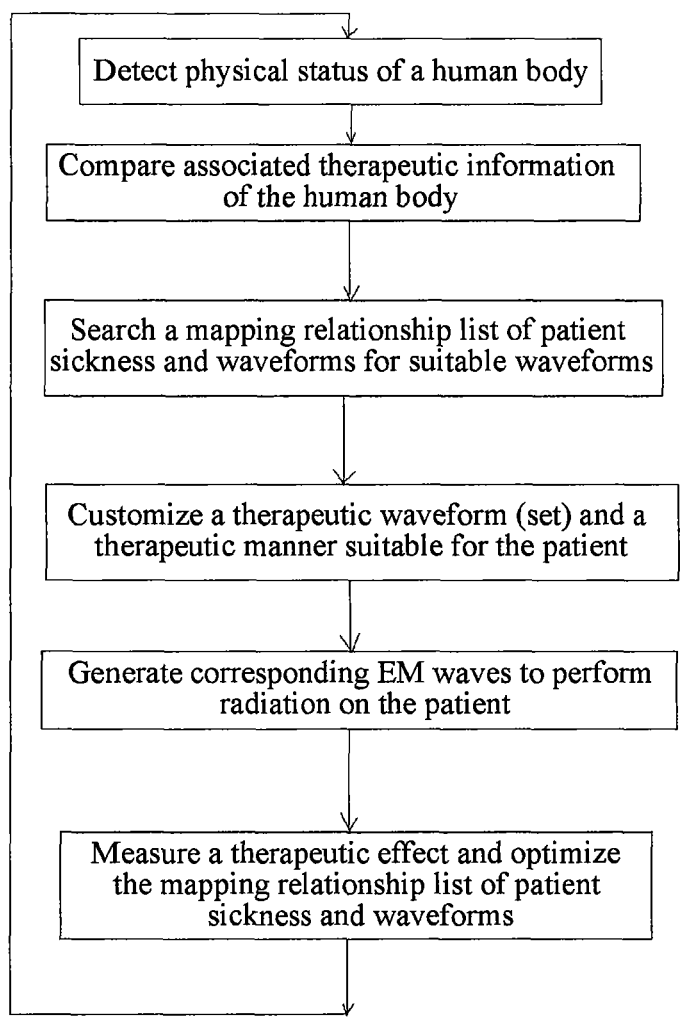
FIG. 4 is a flow chart of operation of a central control unit.

Referring FIG. 4, the central control unit 50 acting as a central control device of the whole therapeutic system controls working of all of the components of the whole system to perform therapy on a patient, and a workflow is as shown below.

In Step 1, work is started.

In Step 2, the heartbeat sensor 58 and the motion sensor 54 are instructed to detect human body status, and send the detected human body status information to the database 11 of the server 1 through the communication module.

In Step 3, comparison is performed on the patient and stored or timely measured other associated therapeutic information, so as to determine sickness.

In Step 4, a therapeutic waveform or waveform combination and a therapeutic means are searched for in the mapping relationship list of patient sickness and waveforms in the database 11 by comparison.

In Step 5, the waveform multiplexer 56 is instructed to output waveform signals, which are respectively input to the driver 561 and/or driver 562, so that the waveform generators 581 and 582 generate a corresponding EM wave or EM wave combination to perform the therapy on the patient in a therapeutic manner, for example, according to a set time period or cycle.

In Step 6, a therapeutic effect is measured and assessed, and data is input to the optimization module 12 to optimize the mapping relationship list of patient sickness and waveforms.

In Step 7, a preferred therapeutic scheme is selected by filtering according to the therapeutic effect of the patient within a certain period of time, and the mapping relationship list of patient sickness and waveforms is optimized.

Figure 5:
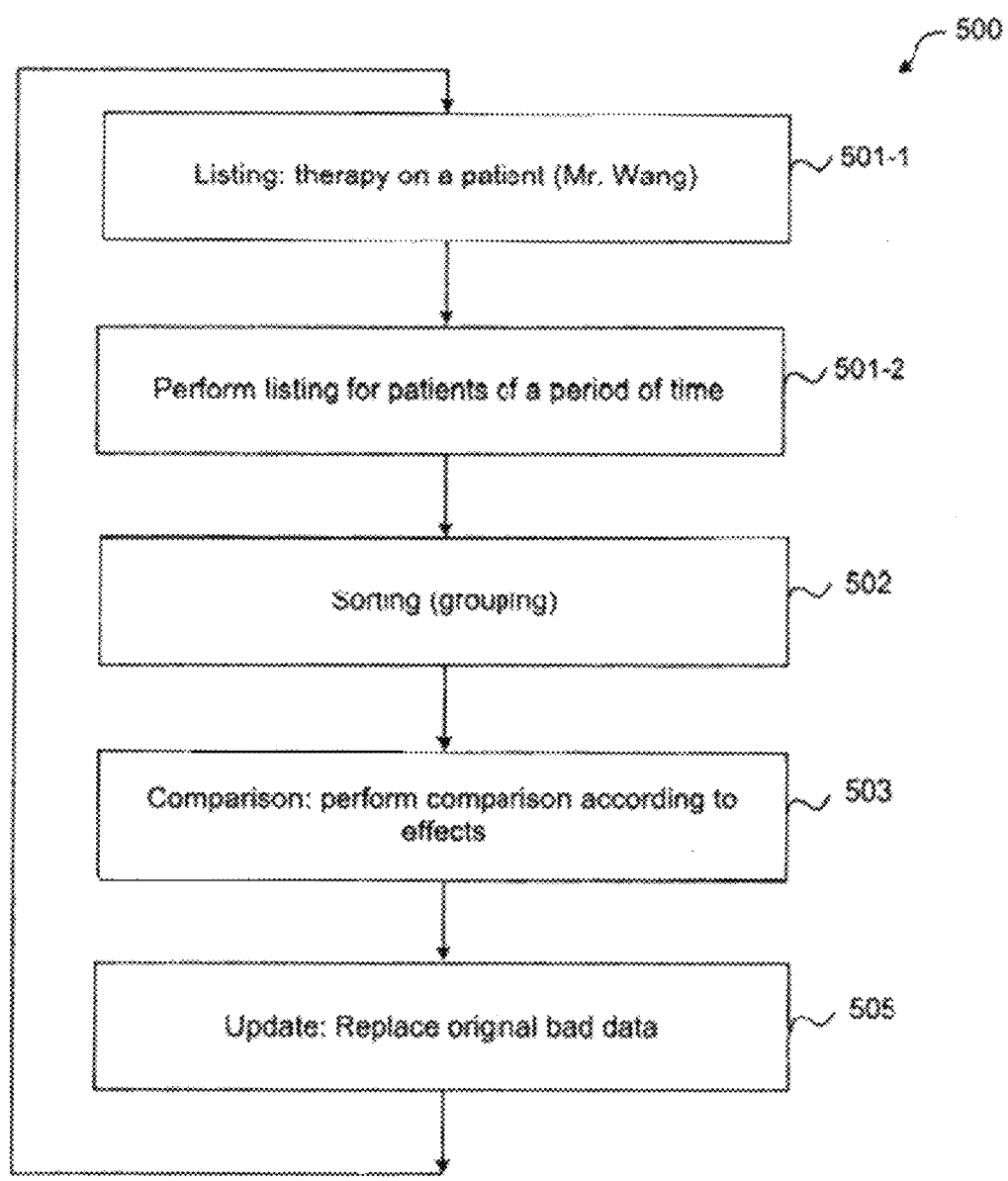
FIG. 5 is an embodiment of an optimization process of a mapping relationship list of patient sickness and waveforms.

FIG. 5 illustrates an embodiment of an optimization process of the "mapping relationship list of patient sickness and waveforms". Referring to FIG. 5, an update process is as follows.

Listing is performed as follows. A list is prepared, which includes "sickness", "therapeutic waveforms", "a therapeutic means" of a therapeutic scheme of a patient (for example Mr. Wang) within a period of time (for example 30 days), and therapeutic effects are classified into grades, for example "excellent", "obviously effective", "so-so", and "ineffective", according to recorded human body status information and according to a set standard. Meanwhile, the parameters of various patients (such as Mr. Zhang, and Mr. Li) of a certain period are also listed in the list.

Sorting is performed as follows. For each certain period of time, for example 30 days, data of all patients of the same sickness is grouped in the list, data parameters corresponding to "excellent" and "obviously effective" in each group are selected.

Comparison is performed as follows. The data parameters corresponding to "excellent" and "obviously effective" and selected during the sorting are compared with a therapeutic effect in the current list.

Update is performed as follows. The "therapeutic waveforms" and "therapeutic means" of the sickness corresponding to the compared data parameters being good are used to replace the original "therapeutic waveforms" and "therapeutic means".

The above process may be performed constantly in a circulating and repeating manner.

Functions of the central control unit 50 are already described above clearly. However, for persons of ordinary skill in the art, the central control unit 50 as a functional component may be disposed in the cell excitation terminal 5, or separately disposed in the server 1, or integrated together with other component, for example, the database 11.

FIG. 6 is a schematic view of an embodiment of the mapping relationship list of patient sickness and waveforms. The list is formed by "sickness", "therapeutic waveforms", and "therapeutic means". The sickness is in a left column, and involves various sickness capable of being treated, for example, a heart disease, a high blood pressure, high cholesterol, and a headache. The heart disease may be divided into heart diseases A1 and A2 according to ages and the sickness. The high blood pressure may also be divided into high blood pressures B1, B2, and B3 according to ages and sickness. A middle column indicates therapeutic waveforms including P1, P2, and P8, which may be a single waveform, or a waveform combination of two or three waveforms, and waveform features, such as intensity, of each of the waveforms may not be the same. A right column indicates a therapeutic manner or means, for example therapeutic manners such as a continuous therapeutic period of time including T1, T2, T3, and T4, an intermittent therapeutic cycle including S1, S2, and S3, and a frequency indicating cross-use of various waveform combinations. According to the list shown in FIG. 6, the central control unit 50 can customize a preferred therapeutic manner corresponding to certain sickness according to information such as physical status of a patient. Therefore, it can be seen that the therapeutic manner can guarantee that a preferred therapeutic effect can be achieved by combining the time, cycle, and frequency and by radiation of various therapeutic waveforms and therapeutic waveform combinations. As aforementioned, the therapeutic manner also results from the optimized mapping relationship list of patient sickness and waveforms. The optimization is constant update and optimization based on assessment, feedback, and filtering performed on several therapeutic schemes, thereby constantly optimizing the therapeutic effect and ensuring the therapeutic effect to be reliable and accurate, which is a major difference between the present invention and the prior art, makes a breakthrough in the EM radiation therapeutic manner and a therapeutic effect of the EM radiation therapeutic manner, and is achieved through creative efforts of the inventors of the present invention.

Figure 7:
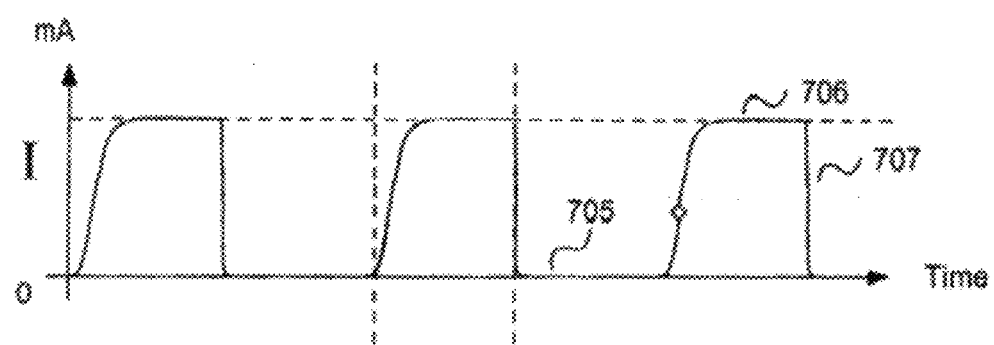
FIG. 7 is a view of a waveform of an EM wave having preferred therapeutic effect.

The therapeutic bioelectromagnetic waveform according to the present invention depends on the sickness of the patient and various pieces of human body status information. The waveforms have different shapes, cycles, and intensity, which are all listed in the mapping relationship list of patient sickness and waveforms and are definitely updated from time to time. The waveform shown in FIG. 7 is a result from therapy performed in a certain period of time in respect of various sickness, shown in FIG. 8A and FIG. 8B, such as a headache, stomach ache, cold, cough, insomnia, and lumbago. According to the therapeutic result, an embodiment of the waveform shown in FIG. 7 has an obvious therapeutic effect on headache, lumbago, and cold, thereby being "obviously effective" (achieving an obvious effect).

In addition, in an embodiment, a therapeutically effective waveform generated by the waveform generator is:

$$I(t) = \begin{cases} 0, & t < 0 \\ I_{max} \times (1 - (1/e^{t/\tau})), & 0 \leq t \leq t_1 \\ 0, & t > t_1 \end{cases}$$

where
a) 300 μsec≤τ≤0.02 sec
b) 5 msec≤$t_1$≤0.1 sec
and
τ is a time constant of generation of the waveform generator,
t is any time point,
($t_1$−t) is a duration or on-time of a pulse, and
$I_{max}$ is a maximum direct current (DC) following in the circuit.

FIG. 9 is a comparison diagram of effects on blood before and after a therapeutic scheme according to the present invention is implemented. In FIG. 9, a comparison diagram of blood before the therapy and after the therapeutic system according to the present invention is applied for 8 minutes is show through three cases. It can be seen from the blood diagrams on the left before the therapy that many red blood cells congregate, and on the right side after 8 minutes of the therapy the red blood cells disperse relatively and seldom congregate.

Figures 1, 10A:
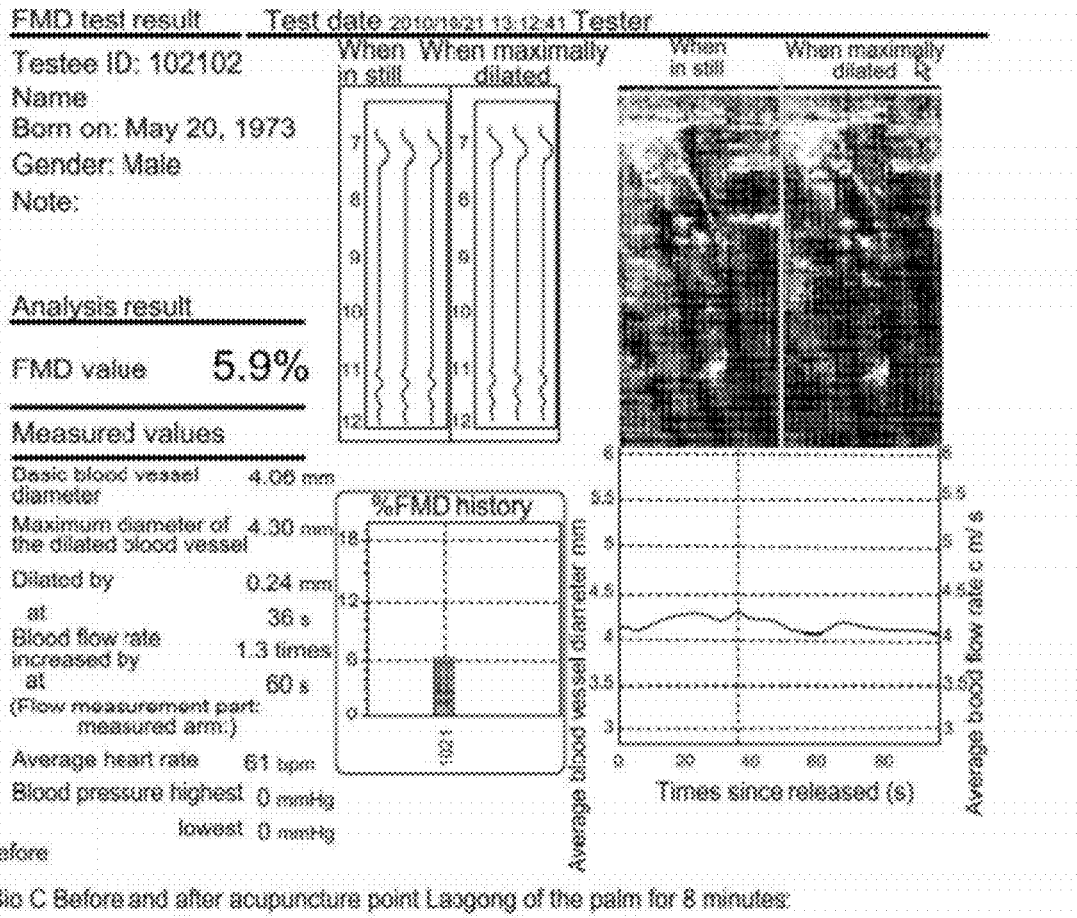
FIG. 10A and FIG. 10B are comparison diagrams of measured effects after a therapeutic scheme is applied on a specific treated part for a certain period of time.
Figures 2, 10A:
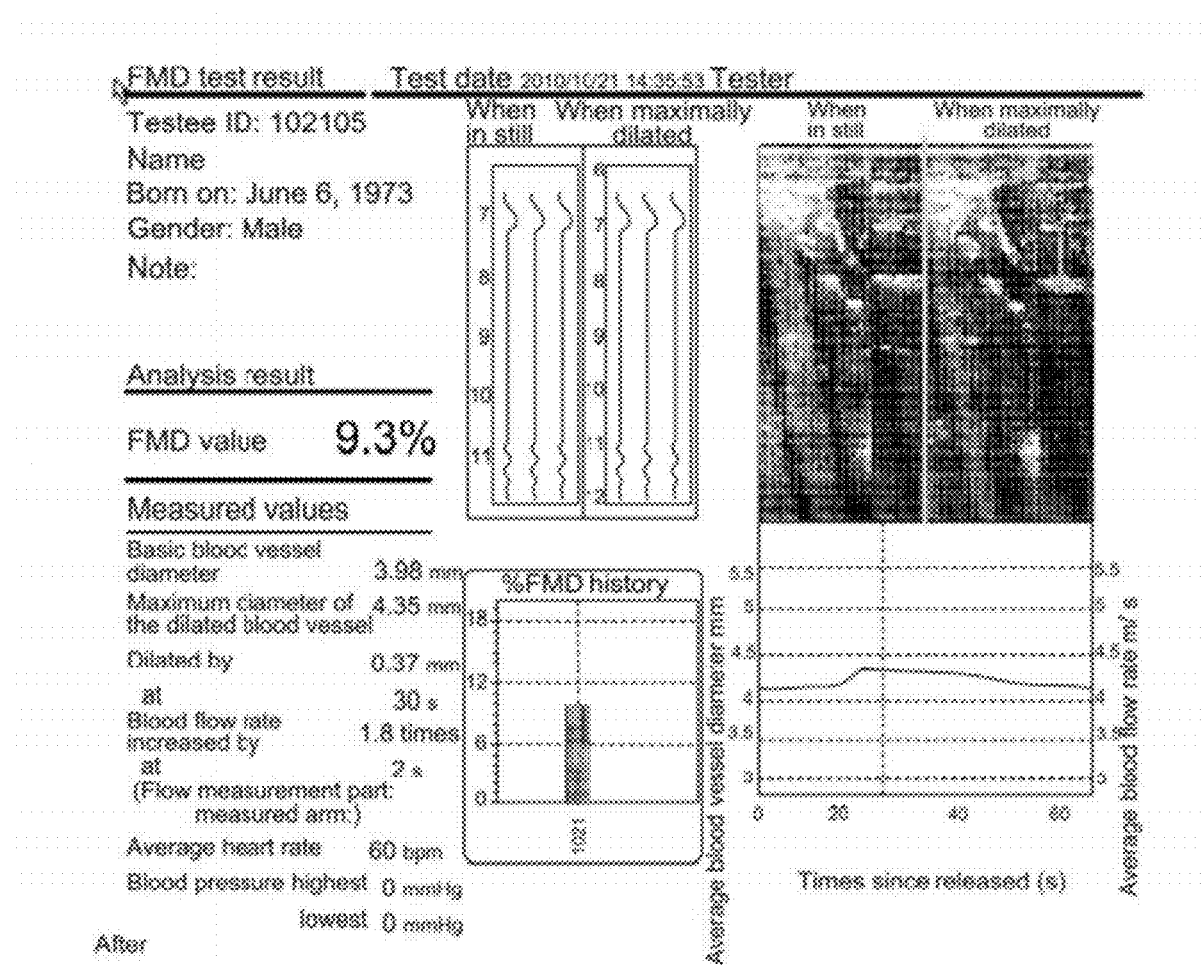
Figures 1, 10B:
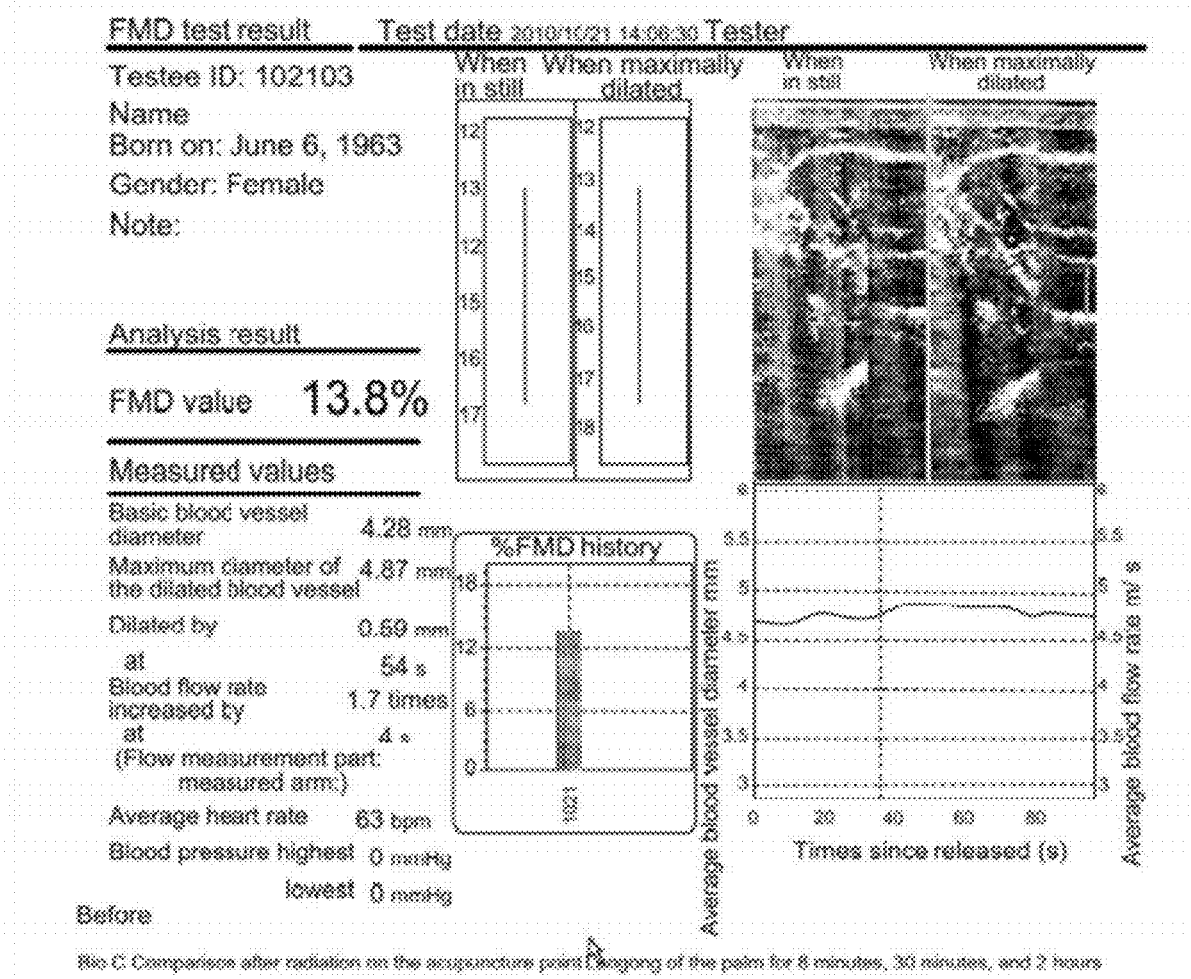
Figures 2, 10B:
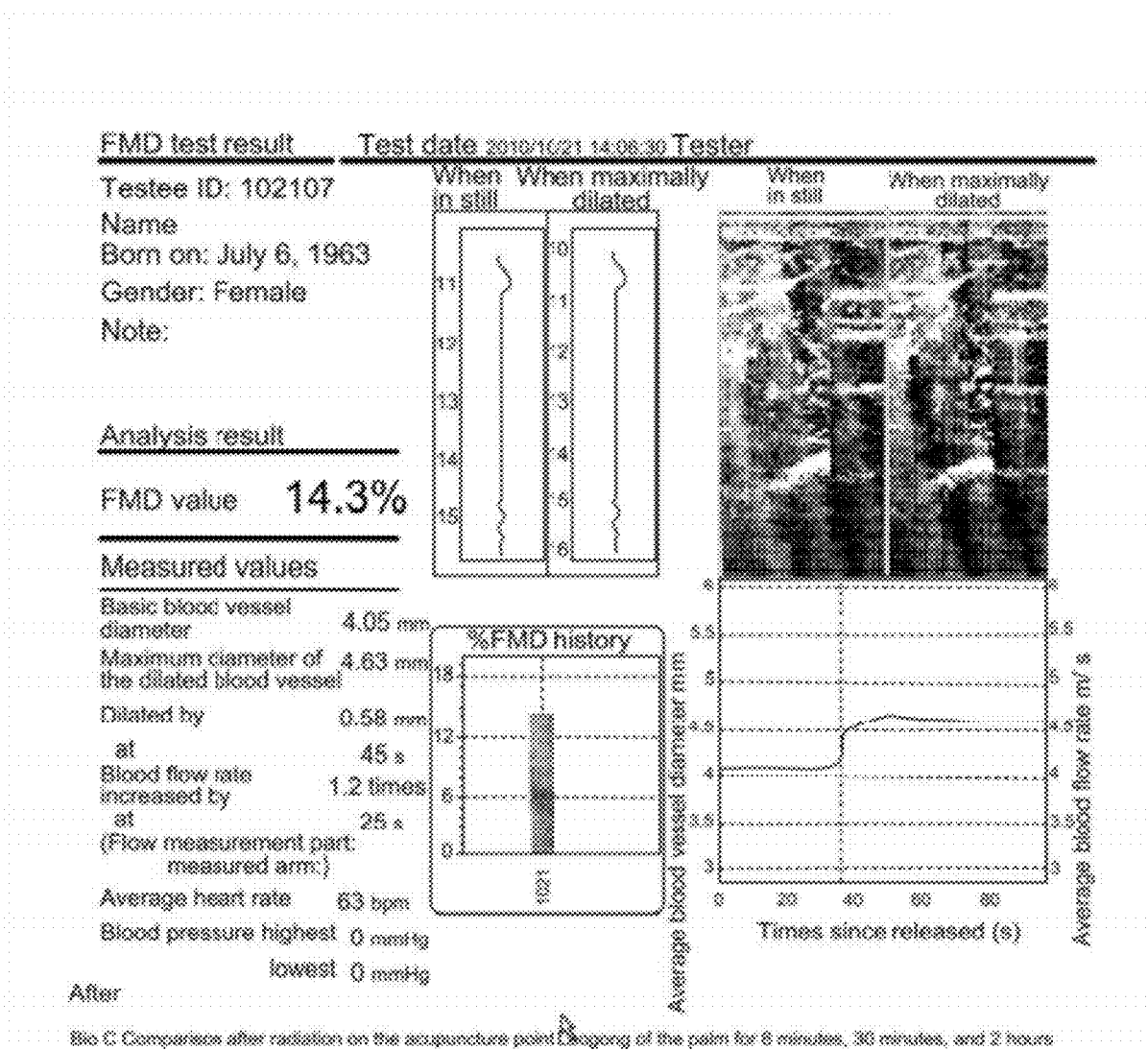

FIG. 10A and FIG. 10B are effect comparison diagrams of brachial artery flow mediated dilation (FMD) and relevant blood properties tested after a therapeutic scheme is applied on a specific treated part, an acupuncture point of a palm and named Laogong, for 8 minutes, 30 minutes, and 2 hours. It is know that the value of the FMD indicates performance of an endothelium. In FIG. 10A, for a patient, after 8 minutes the FMD increases from 5.9% to 9.3%, and blood parameters also improve obviously. In FIG. 10B, for another patient, after 2 hours the FMD increases from 13.8% to 14.3%, and blood parameters also improve obviously.

It can be seen from data analysis according to FIG. 7 to FIG. 10 that, the therapeutic scheme according to the present invention actually achieves an obvious technical effect.

In an embodiment of the present invention, the cell excitation terminal 5 may be used as a separate component to operate, and the server 1 is not needed. In this case, the CPU 50 can control the whole device to perform therapy on a patient, meanwhile the database 11 of the server 1 and other functional modules are integrated in the cell excitation terminal 5 or the CPU 50, and when the cell excitation terminal 5 works alone, and the cell excitation terminal 5 may be provided with generation, storage, and downloading of new and modified encoded data waveforms (which therefore may be applied to the patient) anytime anywhere through a cell phone network or other wired or wireless communication network, thereby also achieving the objective of the present invention.

A working process of the therapeutic system according to the present invention is described below in detail with reference to the accompanying drawings.

First, the cell excitation terminal 5 is fixed on a part of a human body, for example, an acupuncture point of an arm. The cell excitation terminal 5 is very small, and therefore is very easy to be fixed. In this case, once the cell excitation terminal 5 starts working, the heartbeat sensor 58 and the motion sensor 54 detect human body status information constantly, and send the human body status information to the CPU 50. Then, the human body status information is sent to the database of the remote server 1 through the public wireless network to be stored. According to the human body status information and stored or timely measured other physical status parameter data, a corresponding bioelectromagnetic wave (information) and therapeutic manner is selected for the patient from the mapping relationship list of patient sickness and waveforms. The CPU 50 of the cell excitation terminal 5 controls the waveform multiplexer 56, the drivers 561 and 562, and the waveform generators 581 and 582 connected to the drivers 561 and 562 to generate the corresponding bioelectromagnetic wave and use the therapeutic method to perform therapy on the patient directly. In addition, during the therapeutic process, the cell excitation terminal 5 further detects the human body status information of the patient constantly, and transfers the information to the CPU 50 and the remote server timely, so as to timely adjust, select, or change the bioelectromagnetic wave for radiation therapy.

In addition, after the therapy is completed, the EM wave, the therapeutic means, and a therapeutic effect (which can be reflected by or analyzed from the detected human body status information or other test information) of the therapy are sent to the server 1 to be stored. After the number of the patients reaches a certain value, the optimization module of the remote server may update the mapping relationship list of patient sickness and waveforms with the waveform and therapeutic means corresponding to, for example, the "excellent" therapeutic effect among the therapeutic effects. In this way, the patient may receive EM radiation updated from time to time, thereby guaranteeing constant optimization of the therapeutic effect, and meeting requirements from ever changing physical status of the human body.

In addition, the therapeutic system according to the present invention may be controlled remotely, so that the therapeutic EM waves may be timely adjusted or changed during the therapeutic process of the patient, so as to be adapted for various changes of the human body timely.

In an embodiment of the present invention, timely change of the therapeutic EM wave may further improve the therapeutic effect. Examples are provided below.

(1) An EM wave therapeutic manner being used may also vary according to situations. For example, by sensing a heartbeat or pulse frequency of a patient, the heartbeat frequency of the patient is used to directly synchronize or change a specific EM pulse or a set of EM pulses within a period of time before, during, and/or after a heartbeat or local blood pressure pulse, or instead the sensed heartbeat frequency is used to determine when and where changing or replacement is performed by using a different or modified EM pulse or EM pulse set. For example, in a non-limiting example, a selected first wave and specific waveform properties thereof may be used to change the EM wave by a certain manner, for example, by changing a waveform shape and/or frequency components, an amplitude, or other properties between heartbeats or blood pressure pulses but at time corresponding to the heartbeats or local blood pressure pulses, which may be a change applied to only modify the EM pulse at a rate being 30 Hz (30 times per second) corresponding to or synchronized with the heartbeats (for example, 60 to 120 heartbeats per minute), or may be used to preset or dynamically determine the number of the EM pulses, or preset or dynamically determine a time period at or approximately at the heartbeat or the blood pressure pulse.

(2) In a manner, a device is used to modify an EMF, or modify only a magnetic field, or modify only an electric field based on timely human body status information of a patient, for example a response to an EMF (for example a heartbeat frequency or a heart rhythm change), so as to achieve a desired effect, thereby further improving the therapeutic effect. For example, heartbeats, the heat rhythm, and/or, for example, other heart-related patterns acquired from an ECG are used as feedback of the system according to the present invention. Optionally, an extra sensor device is disposed in portable equipment or separately to sense other body symptoms of a patient. For example, an EEG may be acquired from a human body, particularly from a head area of a patient or a person undergoing therapy.

According to the present invention, the EM wave generators are set by configuring to be able to use a relatively low-frequency pulsed magnetic field to stimulate blood circulation in a body of a patient. The low frequency normally ranges from 10 Hz to 200 Hz, typically ranges from 20 Hz to 120 Hz, more typically ranges from 20 Hz to 40 Hz, and is about or actually 30 Hz (for example, 30±3 Hz) in a specific case.

In addition, the present invention can enable therapist, for example medical personnel (or persons in charge of therapy on themselves) to modify the waveform and frequency of the magnetic field and the shape and amplitude of the waveform to be adapted for diagnosis of a patient. Various waveforms may also be applied alternately, and waveforms applied to a part of the body or meridians of the patient may be different from waveforms applied to a different part of the body or meridians of the patient. In addition, when multiple sets of portable equipment are available, the multiple sets of portable equipment can use the same or typically different waveforms and waveforms capable of being dynamically modified, which are applied to different parts or different meridians of the human body at the same time. Furthermore, multiple sets of equipment can be used together with other equipment phased according to a manner, so that only one set or a selected subset of all of the equipment can operate (send electromagnetism or EM radiation) at the same time. Therefore, multiple sets of equipment can be applied to different meridians a single patient and is controlled according to a programmed therapeutic scheme (for example through a timer or local wireless or wired connection) to operate.

The above only shows and illustrates the basic principles, main features, and advantages of the present invention. It should be understood by persons skilled in the art that, the present invention is not limited by the above embodiments, and descriptions of the above embodiments and descriptions in the specification are only intended to illustrate the principles of the present invention. Various modifications and improvements may be made to the present invention without departing from the spirit and scope of the present invention, and all of the modifications and improvements fall within the protection scope of the present invention to be protected. The protection scope of the present invention is defined by the appended claims.

What is claimed is:

1. A handheld cell excitation terminal capable of dynamic optimization of a therapeutic effect, comprising:
    a central processing unit (CPU);
    a human body status detection device, connected to the CPU and used to detect human body status information;
    one or more electromagnetic (EM) wave generators, wherein the one or more EM wave generators are connected to the CPU, and the CPU controls, according to a specific meridian point and a signal detected by the human body status detection device, the one or more EM wave generators to send EM waves corresponding to a detected subject, the EM waves varying dynamically with time for excitation;
    a power device, used to supply power to the handheld cell excitation terminal; and
    the one or more EM wave generators generate a therapeutically effective waveform:

$$I(t) = \begin{cases} 0, & t < 0 \\ I_{max} \times (1 - (1/e^{t/\tau})), & 0 \leq t \leq t_1 \\ 0, & t > t_1 \end{cases}$$

where
a) 300 μsec≤τ≤0.02 sec
b) 5 msec≤$t_1$≤0.1 sec
and
    τ is a time constant of generation of the waveform generator,
    t is any time point,
    ($t_1$-t) is a duration or on-time of a pulse, and
    $I_{max}$ is a maximum direct current (DC) flowing in the circuit.

2. The cell excitation terminal according to claim 1, wherein an EM field (EMF) is a pulsed EMF (PEMF).

3. The cell excitation terminal according to claim 1, wherein the cell excitation terminal further comprises a power monitoring device, sending out a signal to call attention to power supplement, when the power is not enough.

4. The cell excitation terminal according to claim 1, wherein the one or more EM wave generators comprise a waveform multiplexer, selecting corresponding EM waves from the stored waveforms in a server for processing and outputting several required EM waves being the same or different.

5. The cell excitation terminal according to claim 1, wherein the human body status detection device comprises a heartbeat detector.

6. The cell excitation terminal according to claim 1, wherein the human body status detection device comprises a blood pressure detector.

7. The cell excitation terminal according to claim 1, wherein the human body status detection device comprises a motion sensor.

8. The cell excitation terminal according to claim 1, wherein the one or more EM wave generators comprise a drive circuit, receiving a waveform signal from a waveform shaper generator and driving an EM oscillating circuit to generate corresponding EM waves.

9. The cell excitation terminal according to claim 1, wherein the cell excitation terminal comprises a digital-analog (D/A) converter, receiving a digital signal from the CPU and outputting an analog signal to a waveform shaper generator.

10. The remote therapeutic system according to claim 1, wherein the central processing unit works according to the following:
    listing a list of data of sickness, therapeutic waveforms and therapeutic strategies of a therapeutic scheme of a plurality of patients,
    classifying therapeutic effects into a plurality of grades;
    sorting the data of the patients of the same sickness corresponding to a first grade of the grades and a second grade of the grades of the therapeutic; and
    presenting the sorted data of the therapeutic waveforms and therapeutic-strategies of the sickness to the handheld cell excitation.

11. A remote therapeutic system using customized electromagnetic (EM) waves varying dynamically with time for excitation, comprising:
- a central processing unit (CPU);
- a cell excitation terminal, wherein the cell excitation terminal comprises:
  - a human body status detection device, used to detect human body status information;
  - one or more EM wave generators, wherein the one or more EM wave generators are connected to the CPU, and the CPU controls, according to a specific meridian point and a signal detected by the human body status detection device, the one or more EM wave generators to send EM waves corresponding to a detected subject, the EM waves varying dynamically with the time for excitation; and
  - a power device, used to supply power to the cell excitation terminal;
- a server, wherein the server is connected to the cell excitation terminal through a wireless network, wherein the server receives and processes the human body status information sent by the cell excitation terminal, and wherein the server sends an instruction, so that the CPU of the cell excitation terminal controls the one or more EM wave generators to send the EM waves corresponding to the detected subject; and
- the one or more EM wave generators generate a therapeutically effective waveform:

$$I(t) = \begin{cases} 0, & t < 0 \\ I_{max} \times (1 - (1/e^{t/\tau})), & 0 \le t \le t_1 \\ 0, & t > t_1 \end{cases}$$

where
a) 300 μsec≤τ≤0.02 sec
b) 5 msec≤$t_1$≤0.1 sec
and
- τ is a time constant of generation of the waveform generator,
- t is any time point,
- ($t_1$-t) is a duration or on-time of a pulse, and
- $I_{max}$ is a maximum direct current (DC) flowing in the circuit.

12. The remote therapeutic system according to claim 11, wherein the server comprises a database, the database is used to store the detected human body status information, associated therapeutic information, various therapeutic waveforms, and a mapping relationship list of patient sickness and waveforms, the mapping relationship list lists therapeutic EM waves or EM wave combinations and therapeutic strategies corresponding to different human body statuses.

13. The remote therapeutic system according to claim 12, wherein the server further comprises an optimization module, updating the mapping relationship list of patient sickness and waveforms from time to time, so as to update the relationship list with optimal therapeutic EM waves.

14. The remote therapeutic system according to claim 13 wherein the central processing unit works according to the following:
- detecting the human body status by receiving signals from a heartbeat sensor and a motion sensor;
- sending detected human body status information to the database of the server through a communication module;
- determining sickness according to stored or timely measured therapeutic information;
- searching in the mapping relationship list for a therapeutic waveform or waveform combination and the therapeutic strategies in the database;
- outputting waveform signals by a waveform multiplexer for the one or more EM wave generators to generate the corresponding EM wave or EM wave combination to perform a therapy on a patient according to a set time period or cycle;
- obtaining data by measuring and assessing a therapeutic effect to optimize the mapping relationship list; and
- selecting a preferred therapeutic scheme according to the therapeutic effect, and optimizing the mapping relationship list accordingly.

15. The remote therapeutic system according to claim 11, wherein an EM field (EMF) is a pulsed EMF (PEMF).

16. The remote therapeutic system according to claim 11, wherein the human body status detection device comprises a motion sensor.

17. The remote therapeutic system according to claim 11, wherein the EM one or more wave generators comprise a drive circuit, receiving a waveform signal from a waveform shaper generator and driving an EM oscillating circuit to generate corresponding EM waves.

18. The remote therapeutic system according to claim 11, wherein the central processing unit works according to the following:
- listing a list of data of sickness, therapeutic waveforms and therapeutic strategies of a therapeutic scheme of a plurality of patients;
- classifying therapeutic effects into a plurality of grades;
- sorting the data of the patients of the same sickness corresponding to a first grade of the grades and a second grade of the; and
- presenting the sorted list of the therapeutic waveforms and therapeutic-strategies of the sickness to the cell excitation terminal.

19. A remote therapeutic system using customized electromagnetic (EM) waves varying dynamically with time for excitation, comprising:
- a central processing unit (CPU);
- a cell excitation terminal, wherein the cell excitation terminal comprises:
  - a human body status detection device, used to detect human body status information;
  - a communication module to connect to a server through a common wireless communication network or Internet;
  - one or more EM wave generators, wherein each of the one or more EM wave generators is connected to the CPU, and the CPU controls, according to a signal detected by the human body status detection device, the EM wave generators to send EM waves corresponding to a detected subject;
  - a power device, used to supply power to the handheld cell excitation terminal;
- the server, wherein the server is connected to the cell excitation terminal through a wireless network, receives and processes the human body status information sent by the cell excitation terminal, and sends an instruction, so that the CPU of the cell excitation terminal controls the EM wave generator to send the EM waves corresponding to the detected subject; and the server further comprises a database, the database is used to store the detected human body status information, associated therapeutic information, various therapeutic waveforms, and a mapping relationship list of patient sickness and waveforms, the mapping relationship list lists therapeutic EM waves or EM wave combinations and therapeutic strategies corresponding to different human body statuses; and the one or more EM wave generators generate a therapeutically effective waveform:

$$I(t) = \begin{cases} 0, & t < 0 \\ I_{max} \times (1 - (1/e^{t/\tau})), & 0 \leq t \leq t_1 \\ 0, & t > t_1 \end{cases}$$

where
a) 300 μsec ≤ τ ≤ 0.02 sec
b) 5 msec ≤ $t_1$ ≤ 0.1 sec
and
  τ is a time constant of generation of the waveform generator,
  t is any time point,
  ($t_1$-t) is a duration or on-time of a pulse, and
  $I_{max}$ is a maximum direct current (DC) flowing in the circuit.

20. A remote therapeutic system using customized electromagnetic (EM) waves varying dynamically with time for excitation, comprising:
  a central processing unit (CPU);
  a cell excitation terminal, wherein the cell excitation terminal comprises:
    a human body status detection device, used to detect human body status information;
    a communication module to connect to a server through a common wireless communication network or Internet;
    one or more EM wave generators, wherein each of the one or more EM wave generators is connected to the CPU, and the CPU controls, according to a signal detected by the human body status detection device, the EM wave generators to send EM waves corresponding to a detected subject;
    a power device, used to supply power to the handheld cell excitation terminal;
  the server, wherein the server is connected to the cell excitation terminal through a wireless network, receives and processes the human body status information sent by the cell excitation terminal, and sends an instruction, so that the CPU of the cell excitation terminal controls the EM wave generator to send the EM waves corresponding to the detected subject, and wherein an EM field (EMF) is a pulsed EMF (PEMF); and the one or more EM wave generators generate a therapeutically effective waveform:

$$I(t) = \begin{cases} 0, & t < 0 \\ I_{max} \times (1 - (1/e^{t/\tau})), & 0 \leq t \leq t_1 \\ 0, & t > t_1 \end{cases}$$

where
a) 300 μsec ≤ τ ≤ 0.02 sec
b) 5 msec ≤ $t_1$ ≤ 0.1 sec
and
  τ is a time constant of generation of the waveform generator,
  t is any time point,
  ($t_1$-t) is a duration or on-time of a pulse, and
  $I_{max}$ is a maximum direct current (DC) flowing in the circuit.

* * * * *